United States Patent
Hall et al.

(10) Patent No.: US 9,034,943 B2
(45) Date of Patent: May 19, 2015

(54) SALTS OF DEHYDROACETIC ACID AS A PYRITHIONE STABILIZER IN PLASTICS

(75) Inventors: Larry Kent Hall, Easton, PA (US); Joseph Kimler, Yardville, NJ (US); Lei Rao, Highland Mills, NJ (US)

(73) Assignee: LONZA LTD, Basel (CH)

( * ) Notice: Subject to any disclaimer, the term of this patent is extended or adjusted under 35 U.S.C. 154(b) by 0 days.

(21) Appl. No.: 13/258,874

(22) PCT Filed: Mar. 26, 2010

(86) PCT No.: PCT/EP2010/001935
§ 371 (c)(1),
(2), (4) Date: Sep. 22, 2011

(87) PCT Pub. No.: WO2010/108695
PCT Pub. Date: Sep. 30, 2010

(65) Prior Publication Data
US 2012/0015986 A1 Jan. 19, 2012

Related U.S. Application Data

(60) Provisional application No. 61/163,505, filed on Mar. 26, 2009.

(51) Int. Cl.
*A01N 43/40* (2006.01)
*A01N 25/22* (2006.01)

(52) U.S. Cl.
CPC .................................. *A01N 43/40* (2013.01)

(58) Field of Classification Search
None
See application file for complete search history.

(56) References Cited

U.S. PATENT DOCUMENTS

2009/0203812 A1* 8/2009 Rao et al. ...................... 523/122

FOREIGN PATENT DOCUMENTS

JP          2002020207 A  *  1/2002  ............. A01N 43/16

* cited by examiner

*Primary Examiner* — James J Seidleck
*Assistant Examiner* — Peter A Salamon
(74) *Attorney, Agent, or Firm* — Hoffmann & Baron, LLP

(57) ABSTRACT

The invention provides a method for preventing discoloration of pyrithione-containing materials, in particular plastic materials or other material such as paints, coatings, adhesives or textiles which are exposed to an outdoor environment. The method is likewise suited for preventing discoloration of other pyrithione-containing materials such as personal care compositions like shampoos. A discoloration inhibitor that includes dehydroacetic acid or a salt thereof is added to the pyrithione-containing material. The discoloration is prevented without the addition of a cyclic organic phosphoric acid ester or an organic phosphite. Use of the discoloration inhibitor does not interfere with the antimicrobial effect of the pyrithione.

12 Claims, No Drawings

SALTS OF DEHYDROACETIC ACID AS A PYRITHIONE STABILIZER IN PLASTICS

This application is the U.S. National Phase of, and Applicants claim priority from, International Patent Application Number PCT/EP2010/001935 filed Mar. 26, 2010, and U.S. Provisional Patent Application bearing Ser. No. 61/163,505 filed Mar. 26, 2009, which are incorporated herein by reference in their entirety.

BACKGROUND OF THE INVENTION

The present invention relates to inhibiting discoloration of products that contain pyrithione, in particular products that are exposed to weathering conditions.

Depending on their use, products such as plastics, especially those which are exposed to weathering conditions, require use of antimicrobials. A common antimicrobial used in plastics is pyrithione, and especially zinc pyrithione. Unfortunately, plastic materials containing zinc pyrithione tend to discolor.

U.S. Pat. No. 4,348,308 discloses using dehydroacetic acid (DHA) or its salts and ortho-tertiary-alkyl substituted phenyl phosphite as an additive composition for improving the color stability of a vinyl chloride polymer. The compositions do not include an antimicrobial.

U.S. Pat. No. 4,301,162 discloses the use of dehydroactic acid and its alkali salts in combination with 2-pyridinethiol 1-oxide (pyrithione) and its salts as anti-bacterial and anti-fungal agents for industrial and agricultural products including plastic moldings, etc. U.S. Pat. No. 4,301,162 does not disclose the discoloration of plastics caused by pyrithione and its salts nor does it disclose the effects of outdoor weathering conditions on plastics containing pyrithione and its salts.

JP 09-087229 A discloses an antibacterial composition formed by the addition of a cyclic organic phosphoric ester compound and dehydroacetic acid or metal salts thereof to a polymeric material. According to JP 09-087229 A, a specific acidic organic phosphoric acid ester or its metal salt along with a dehydroacetic acid compound resulted in excellent antimicrobial properties, heat resistance, stability in water or oil, and did not possess any discoloration. JP 09-087229 A lists numerous additional antibacterial and antifungal compounds that may be added to the polymeric material, including 2-pyridinethiol 1-oxide and its salts. JP 09-087229 A does not discuss discoloration of plastic materials exposed to outdoor weathering conditions.

There is an ongoing need for an effective means of preventing discoloration of materials, in particular plastic materials, containing a pyrithione antimicrobial.

SUMMARY OF THE INVENTION

The present invention relates to a method for inhibiting discoloration of a material that contains pyrithione or a salt thereof. According to the method, an effective amount of a discoloration inhibitor which includes dehydroacetic acid (DHA) or a salt thereof is added to the material.

In one preferred embodiment of the method, the material containing pyrithione or a salt thereof is selected from the group consisting of paints, coatings, adhesives, and textiles, and is exposed to outside weathering conditions.

In a second preferred embodiment of the method, the material containing pyrithione or a salt thereof is a personal care formulation, more preferably a shampoo.

In another, particularly preferred embodiment of the method, the material containing pyrithione or a salt thereof is a plastic material that is exposed to outside weathering conditions.

In a preferred embodiment of the method, the discoloration inhibitor is the zinc salt of dehydroacetic acid (zinc dehydroacetate).

More preferably, the material containing pyrithione or a salt thereof is a plastic material that is extruded and the zinc salt of dehydroacetic acid is co-extruded with the plastic material.

The plastic material in the method of the invention does not require, and preferably does not contain, an organic phosphite, a substituted phenyl phosphite, an ortho-substituted phenyl phosphite, or an ortho-tertiary alkyl-substituted phenyl phosphite as an additive.

Likewise, the plastic material in the method of the invention does not require, and preferably does not contain, a cyclic organic phosphoric acid ester as an additive.

In another preferred embodiment, the discoloration inhibitor consists essentially of dehydroacetic acid or a salt thereof, without any additional discoloration inhibitors.

The discoloration inhibitor provides the benefit of preventing discoloration without inhibiting the antimicrobial action of the pyrithione or a salt thereof.

For a better understanding of the present invention, together with other and further objects, reference is made to the following description, taken in conjunction with the examples, and its scope will be pointed out in the appended claims.

DETAILED DESCRIPTION

The invention relates to a method for inhibiting discoloration of a material that is caused by the presence of pyrithione or a salt thereof.

In one preferred embodiment of the method, the material containing pyrithione or a salt thereof is selected from the group consisting of paints, coatings, adhesives, and textiles, and is exposed to outside weathering conditions.

In a second preferred embodiment of the method, the material containing pyrithione or a salt thereof is a personal care formulation, more preferably a shampoo.

In another, particularly preferred embodiment of the method, the material containing pyrithione or a salt thereof is a plastic material that is exposed or expected to be exposed, to weathering conditions, in particular to outside weathering conditions.

The plastic material can be made from any polymeric material (polymer) that is capable of forming plastics. Some examples of polymers include polyamides, polyacetals, polycarbonates, and polysulfones. Preferably, the polymer is a vinyl polymer. Some examples of vinyl polymers include polyethylene, polypropylene, polyethylene terephthalate, polybutylene terephthalate, polytetrafluoroethylene, polystyrene, polyacrylates, polymethacrylates, polyvinyl alcohol, polyvinyl acetate, polyvinyl chloride, and polyacrylonitrile. Another suitable polymer is polybutadiene. The polymeric plastic materials may be thermoplastic or thermoset.

Plastic materials exposed, or expected to be exposed to outside weathering conditions include all plastic materials intended for outdoor use or exposure to an outside environment. Examples of plastic materials that are exposed, or expected to be exposed, to outside weathering conditions include, for example: playground equipment such as slides, swings, etc.; siding for buildings; roofing materials; automotive parts; doors; trash cans; patio furniture; park benches;

outdoor sports equipment; planters; recycle bins; outdoor hoses; outdoor extension cords; sandboxes; children's wading pools; outdoor children's toys; shoes; and numerous other items.

Outdoor weathering conditions include, for example, sunlight, wind, rain, variations in temperature—both extreme and mild variations, hail, sleet, snow, etc. Other less common outdoor weathering conditions include, for example, sand, dust, or salt water.

Discoloration of a plastic material includes, for example, darkening, yellowing, fading, and any other change of color of the plastic material from the intended color. Discoloration can occur over time or during processing of the plastic material.

The materials treated in accordance with the present invention contain pyrithione or salts thereof as an antimicrobial. Therefore, the pyrithione or its salts are present in an amount sufficient to act as an antimicrobial. For example, the amount of pyrithione or salts thereof may be from about 500 ppm to about 5,000 ppm by weight. Preferably, the amount of pyrithione or its salts is about 1,000 ppm to about 4,000 ppm. Preferably, the pyrithione is a pyrithione salt. Suitable salts of pyrithione include, for example, sodium pyrithione, zinc pyrithione and copper pyrithione. More preferably, the pyrithione salt is zinc pyrithione.

Dehydroacetic acid or a salt of dehydroacetic acid is added to the material, such as plastic material, to prevent the discoloration caused by pyrithione or its salts. Salts of dehydroacetic acid include, for example, lithium dehydroacetate, sodium dehydroacetate, potassium dehydroacetate, magnesium dehydroacetate, calcium dehydroacetate, strontium dehydroacetate, barium dehydroacetate, copper dehydroacetate, and zinc dehydroacetate. Some of these salts, in particular zinc dehydroacetate, form stable hydrates which may be used instead of, or in addition to, the corresponding anhydrous forms. More preferably, the discoloration inhibitor of the invention is the zinc salt, sodium salt, or copper salt of dehydroacetic acid, the zinc salt of dehydroacetic acid being most preferred.

Still more preferably, the material containing pyrithione or a salt thereof is a plastic material that is extruded, and the zinc salt of dehydroacetic acid is co-extruded with the plastic material.

Pyrithione and its salts can be stabilized by dehydroacetic acid and its salts without the addition of an organic phosphite. Organic phosphites include, for example, phenyl phosphites, including diphenyl and/or triphenyl phosphites; substituted phenyl phosphites, including substituted diphenyl and/or triphenyl phosphites; ortho-substituted phenyl phosphites; and ortho-tertiary alkyl-substituted phenyl phosphites.

Pyrithione and its salts can also be stabilized by dehydroacetic acid or its salts without the addition of a cyclic organic phosphoric acid ester.

In another preferred embodiment, the discoloration inhibitor consists essentially of dehydroacetic acid or a salt thereof, without any additional discoloration inhibitors.

The dehydroacetic acid or salts thereof and pyrithione or salts thereof can be added to the plastic any time before, during or after processing. The dehydroacetic acid or salts thereof and pyrithione or salts thereof can be added to the polymeric material in any order. For example, the pyrithione or its salts may be added first, the dehydroacetic acid or its salts may be added first, or the pyrithione or its salts and dehydroacetic acid or salts thereof may be added to the polymeric material simultaneously.

An effective amount of dehydroacetic acid or a salt thereof, is an amount sufficient to prevent discoloration of a material, such as a plastic material, caused by pyrithione or a salt thereof. For example, an effective amount can include from about 0.05% to about 5% by weight (about 500 to about 50,000 ppm), preferably from about 0.1% to about 5% (about 1,000 to about 50,000 ppm), more preferably from about 0.2% to about 4% (about 2,000 to about 40,000 ppm), or from about 1.0% to about 5% (about 10,000 to about 50,000 ppm), in particular greater than 10,000 ppm to about 50,000 ppm of dehydroacetic acid or salt thereof. The percentage amount is based on the total amount of components of the respective material.

The polymeric material can be processed one time or multiple times, prior to, during, or following the addition of the pyrithione or its salts and/or the dehydroacetic acid or salts thereof. Types of processing which the polymeric material, or resulting plastic material can undergo include, for example, blending, extruding, fiber spinning, film blowing, filament winding, spin coating, molding, blow molding, injection molding, reaction injection molding, transfer molding, or combinations of these types of processing.

The polymeric material and the plastic material that includes pyrithione or salts thereof and dehydroacetic acid or salts thereof can undergo the above mentioned processing at suitable temperatures, as is well known in the art. Preferably, the processing steps are performed at temperatures at which the plastic, pyrithione, and DHA are stable. For example, Zn DHA decomposes at about 277° C. For very short processing steps, higher temperatures may be used. For most polymers, processing may be accomplished between 100° C. and 450° C., preferably between 120° C. and 240° C. For PVC, for example, 170° C. up to less than 200° is typical.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g., polymers, dehydroacetic acid and its salts, polymer processing). Each group contains multiple members. For example, polymers include polyethylene, polypropylene, polyvinyl acetate, polyvinyl chloride, etc. Each member may be combined with each other member to form additional sub-groups, e.g., polyethylene and polyvinyl acetate, polypropylene and polyethylene, and polypropylene and polyvinyl acetate.

The instant invention further contemplates embodiments in which each element listed under one group may be combined with each and every element listed under any other group. For example, polymers identified above may represent a vinyl polymer, polyacetal, etc. Dehydroacetic acid and salts thereof, are identified above as representing zinc dehydroacetic acid, copper dehydroacetic acid, dehydroacetic acid, etc. Pyrithione and salts thereof are identified as representing zinc pyrithione, copper pyrithione, etc. Each polymer can be combined with each and every dehydroacetic acid or salt thereof. For example, in one embodiment, the polymer may be a polyacetal; the dehydroacetic acid or salts thereof may be copper dehydroacetic acid; and pyrithione or salts thereof may be zinc pyrithione. Alternatively, the polymer may be a vinyl polymer; the dehydroacetic acid or salts thereof may be dehydroacetic acid; and the pyrithione or salts thereof may be zinc pyrithione. Similarly, a fourth group is the processing methods including blending, extruding, etc. Each of the above embodiments may be combined with each and every processing method. For example, in the embodiment wherein the polymer is a vinyl polymer; the dehydroacetic acid or salt thereof is dehydroacetic acid; and the pyrithione or salts thereof is zinc pyrithione, the processing method may be extruding (or any processing method listed).

With each group, it is specifically contemplated that any one or more members can be excluded. For example, if a polymer is defined as a polyamide, polyacetal, polycarbonate, polysulfone, or vinyl polymer, it is also contemplated that the polymer is defined as polyacetals or polysulfones, or any other combination of two, three, or four polymers.

A list following the word "comprising" is inclusive or open-ended, i.e., the list may or may not include additional unrecited elements. A list following the words "consisting of" is exclusive or closed ended, i.e., the list excludes any element not specified in the list.

All numbers in the specification are approximate unless indicated otherwise.

EXAMPLES

The present invention can be better understood by reference to the following examples. The following examples illustrate the present invention and are not intended to limit the invention or its scope in any manner.

Example 1

Stabilized Zinc Pyrithione:

Zinc dehydroacetate and zinc pyrithione were mixed with filled and clear commercial flexible polyvinyl chloride (PVC) compounds. The mixtures were extruded using an intermeshing modular co-rotating twin screw extruder to form flexible PVC compounds. The extruder had a temperature profile of 140° C., 170° C., 175° C., 175° C., 175° C., and 175° C. at the respective extruder zones. Following extrusion, the flexible PVC compounds were cooled. Once cooling was complete, the flexible PVC compounds were pressed at 185° C. to form plastic sheets.

Example 2

Unstabilized Zinc Pyrithione:

Zinc pyrithione was mixed with filled and clear commercial flexible polyvinyl chloride (PVC) compounds. The mixtures were extruded using an intermeshing modular co-rotating twin screw extruder to form flexible PVC compounds. The extruder had a temperature profile of 140° C., 170° C., 175° C., 175° C., 175° C., and 175° C. at the respective extruder zones. Following extrusion, the flexible PVC compounds were cooled. Once cooling was complete, the flexible PVC compounds were pressed at 185° C. to form plastic sheets.

Example 3

Untreated Control:

Clear and filled commercial flexible polyvinyl chloride (PVC) compounds were extruded using an intermeshing modular co-rotating twin screw extruder to form flexible PVC compounds. The extruder had a temperature profile of 140° C., 170° C., 175° C., 175° C., 175° C., and 175° C. at the respective extruder zones. Following extrusion, the flexible PVC compounds were cooled. Once cooling was complete, the flexible PVC compounds were pressed at 185° C. to form plastic sheets.

Example 4

Stability Evaluation

Plastic sheets from Examples 1-3 were cut into 7.62×15.24 $cm^2$ (3"×6") rectangles and placed in a QUV accelerated weathering tester. The weathering tester was set to a cycle of eight hours of ultraviolet A light (long wave) exposure and a four hour water condensation cycle in accordance with ASTM standard test D154. After 1,000 hours of exposure, the plastic sheets were examined for color development. The results of the discoloration tests are compiled in Table 1 below.

TABLE 1

| Sample | Color Rating of Clear FPVC | | Color Rating of Filled FPVC | |
|---|---|---|---|---|
| | 0 hours | 1,000 hours | 0 hours | 1,000 hours |
| Control (Untreated) | 0 | 0 | 0 | 3 |
| Zinc Pyrithione (2,500 ppm) | 0 | 3 | 0 | 4 |
| Zinc Pyrithione/ Zinc DHA (1,250 ppm each) | 0 | 1 | 0 | 2 |

The color scale is from 0 to 4:
0 - no color change
1 - slightly yellowish
2 - yellowish brown
3 - brown
4 - dark brown A comparison of the untreated control (Example 3) and the unstabilized zinc pyrithione (Example 2) reflects the discoloration caused by unstabilized zinc pyrithione in clear plastic. In filled plastic, the discoloration caused by the unstabilized zinc pyrithione is also shown. Therefore, it is evident that unstabilized zinc pyrithione is capable of discoloring both clear and filled plastic exposed to weathering conditions.

In a comparison of the unstabilized zinc pyrithione (Example 2) with the stabilized zinc pyrithione (Example 1), the stabilized zinc pyrithione results in less discoloration of clear and filled plastic than the unstabilized zinc pyrithione. In the filled plastic, the stabilized zinc pyrithione also results in less discoloration of the plastic than the untreated control. Therefore, it is evident that stabilized zinc pyrithione, which provides an antimicrobial benefit, causes less discoloration of plastic materials than unstabilized zinc pyrithione.

Example 5

Fungal Resistance Test

In accordance with ASTM test method G21, three samples from each of the prepared plastics listed above were placed in Petri dishes on mineral salts agar and inoculated with the following fungi: *Aspergillus niger* ATCC 9642; *Aureobasidium pullulans* ATCC 15233; *Chaetomium globosum* ATCC 6205; *Penicillium funiculosum* ATCC 11797; and *Trichoderma virens* ATCC 9645. The sample designated "unstabilized zinc pyrithione" contained 2,500 ppm zinc pyrithione while stabilized sample contained 1,250 ppm zinc pyrithione and 1,250 ppm zinc dehydroacetate. The samples were incubated at 28° C. for 4 weeks. The samples were examined weekly for growth of test organisms. The results are reflected in Table 2 below.

TABLE 2

| Sample | Total Concentration of Zinc (as Zn, ppm) | Fungal Growth Reading* | Zone of Inhibition** |
|---|---|---|---|
| Untreated Control | 0 | 4 | − |
| Unstabilized Zinc Pyrithione | 515 | 0 | ++ |
| Stabilized Zinc Pyrithione | 445 | 0 | ++ |

*Fungal Growth Rating
None: 0
Traces of growth (<10%): 1
Light growth (10% to 30%): 2
Medium growth (30% to 60%): 3
Heavy growth (>60%): 4
**Zone of Inhibition
No Zone −
Small Zone +
Large Zone ++

As Table 2 above shows, when added to plastic materials containing pyrithione or its salts, dehydroacetic acid or its salts do not interfere with the antimicrobial activity of the pyrithione or its salts.

Thus, while there have been described what are presently believed to be the preferred embodiments of the present invention, those skilled in the art will appreciate other and further changes and modifications thereto, and it is intended to include such other changes as come with the scope of the invention as set forth in the following claims.

The invention claimed is:

1. A method for inhibiting discoloration of a material that comprises pyrithione or a salt thereof, the method comprising adding an effective amount of a discoloration inhibitor comprising dehydroacetic acid or a salt thereof to said material, wherein said material is a plastic material made from a vinyl polymers; wherein said vinyl polymer is selected from the group consisting of polyethylene, polypropylene, polyvinyl acetate, and polyvinyl chloride; and wherein said material is exposed to outside weathering conditions.

2. The method of claim 1 wherein the discoloration inhibitor is the zinc salt of dehydroacetic acid.

3. The method of claim 1 wherein said plastic material is extruded and the zinc salt of dehydroacetic acid is co-extruded with the plastic material.

4. The method of any of claim 1 wherein no organic phosphite is added to the plastic material.

5. The method of claim 1 wherein no substituted phenyl phosphite is added to the plastic material.

6. The method of claim 1 wherein no ortho-substituted phenyl phosphite is added to the plastic material.

7. The method of claim 1 wherein no ortho-tertiary alkyl-substituted phosphite is added to the plastic material.

8. The method of claim 1 wherein no cyclic organic phosphoric acid ester is added to the plastic material.

9. The method of claim 1 wherein the discoloration inhibitor consists essentially of dehydroacetic acid or a salt thereof.

10. The method of claim 1 wherein said discoloration inhibitor is added in an amount sufficient to provide a concentration of 500 ppm to 50,000 ppm by weight of dehydroacetic acid or salt thereof.

11. The method of claim 10, wherein said discoloration inhibitor is added in an amount sufficient to provide a concentration of 10,000 ppm to 50,000 ppm by weight of dehydroacetic acid or salt thereof.

12. The method of claim 1 wherein said polymer is polyvinyl chloride.

* * * * *